United States Patent
Keller et al.

[11] Patent Number: 6,143,850
[45] Date of Patent: Nov. 7, 2000

[54] LIPOPHILIC POLYMERIC UV ABSORBERS

[75] Inventors: Harald Keller, Ludwigshafen; Volker Schehlmann, Römerberg; Horst Westenfelder, Neustadt; Thomas Preiss, Ludwigshafen, all of Germany

[73] Assignee: BASF Aktiengesellschaft, Ludwigshafen, Germany

[21] Appl. No.: 09/131,391

[22] Filed: Aug. 7, 1998

[30] Foreign Application Priority Data

Aug. 8, 1997 [DE] Germany ............ 197 34 445

[51] Int. Cl.$^7$ ................................ C08F 20/58
[52] U.S. Cl. ................ 526/304; 526/305; 526/307
[58] Field of Search ................. 526/305, 307, 526/304

[56] References Cited

U.S. PATENT DOCUMENTS

| | | | |
|---|---|---|---|
| 5,371,148 | 12/1994 | Taylor et al. | 525/293 |
| 5,869,099 | 2/1999 | Keller et al. | 424/486 |
| 5,914,283 | 6/1999 | Yamada et al. | 442/117 |

FOREIGN PATENT DOCUMENTS 672 658  9/1995  European Pat. Off. .

*Primary Examiner*—Edward J. Cain
*Attorney, Agent, or Firm*—Keil & Weinkauf

[57] ABSTRACT

Polymeric UV absorbers based on the units shown in the schematized formula I

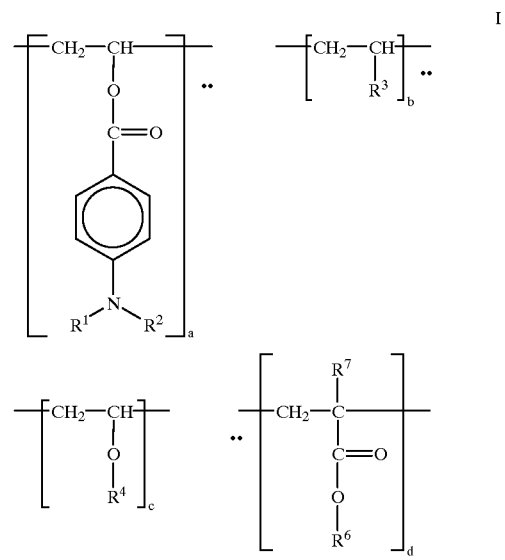

where
the sequence of the units is arbitrary, the sum of $a+b+c+d=100$ and
a is a value from 5 to 95,
b is a value from 0 to 70,
c is a value from 5 to 95,
d is a value from 0 to 70
and the radicals R have the meaning explained in the description, are described.

4 Claims, No Drawings

LIPOPHILIC POLYMERIC UV ABSORBERS

The present invention relates to lipophilic polymeric UV absorbers based on benzoic acid derivative chromophores and cosmetic compositions with polymer-bound benzoic acid chromophores for protecting the skin and the hair from UV radiation.

A good water resistance is often desirable in the case of cosmetic sunscreen compositions which are applied to the skin. This property is particularly required if more frequent contact of the skin with water or aqueous fluids such as perspiration takes place. In order to achieve the required water resistance, polymers are often added to such compositions.

A further possibility consists in linking the UV-absorbing groups covalently to a polymer.

WO 89/4824 describes copolymers of the UV-absorbing styrene and maleic anhydride, vinylpyrrolidone or acrylates. These copolymers have a high water solubility and a low skin penetration.

JP 60/88066 describes UV-absorbing benzophenone derivatives which are bound to (meth)acrylates via a urethane spacer. These polymers are suitable as a material for contact lenses and spectacle lenses.

EP 123 368 describes polymeric sunscreen compositions which are synthesized from the following monomers:
(a) an olefinic p-aminobenzoic acid ester,
(b) N-vinylpyrrolidone and
(c) a vinyllactam, acrylate or methacrylate and also mixtures thereof.

JP 03220213 describes polymeric UV absorbers formed from:
(a) vinyl N,N-dimethylaminobenzoate,
(b) methyl methacrylate,
(c) styrene,
(d) hydroxybutyl vinyl ether,
(e) methacrylic acid and
(f) divinylbenzene.

Beside the good water resistance, the cosmetic compositions, however, should satisfy a number of other properties such as low skin penetration, low content of residual monomers, which are to be avoided for toxicological and olfactory reasons, and good processability, miscibility and stability with other components of cosmetic compositions.

Additionally, the polymeric UV absorbers should have a high extinction in the UV range as well as a good oil solubility.

We have found lipophilic polymeric UV absorbers having the units shown in the schematized formula I

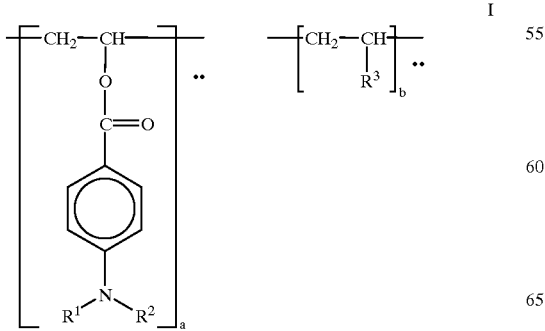

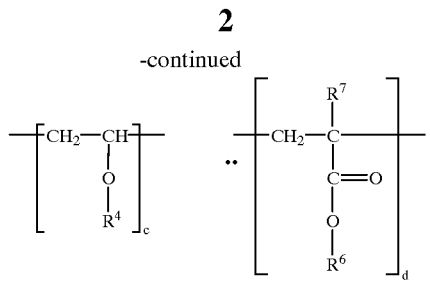

where the sequence of the units is arbitrary, the sum of a+b+c+d=100 and
a is a value from 5 to 95,
b is a value from 0 to 70,
c is a value from 5 to 95,
d is a value from 0 to 70
$R^1$, $R^2$ independently of one another are H, $C_1$–$C_8$-alkyl
$R^3$ is

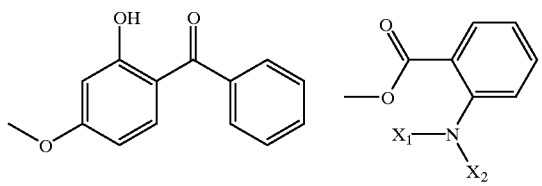

$X^1$, $X^2$ independently of one another are H, $C_1$–$C_8$-alkyl,

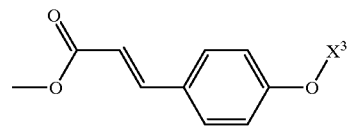

$X^3$ is H, $C_1$–$C_8$-alkyl,

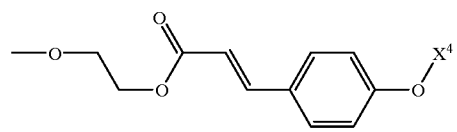

$X^4$ is H, $C_1$–$C_8$-alkyl,

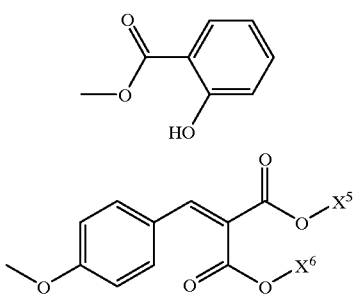

$X^5$, $X^6$ independently of one another are H, $C_1$–$C_8$-alkyl,

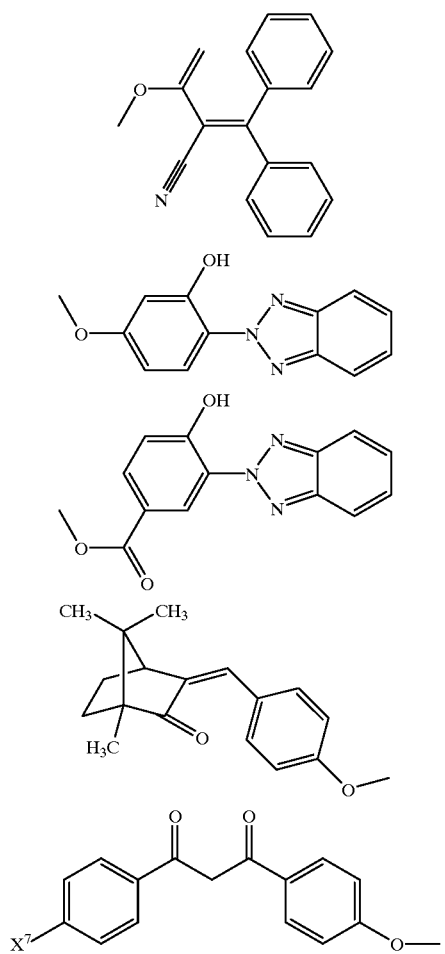

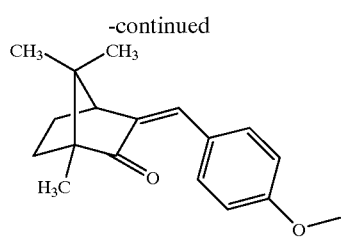

The preparation of the monomers for the unit b is known or is easy to carry out for the person skilled in the art from similar reactions.

The preparation of the monomers of the formula II

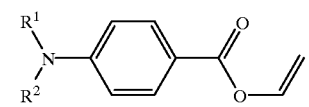

II is described in U.S. Pat. No. 661,005 and FR 691 020.

The preparation of the monomers of the formula IV

IV where $R^3$ is

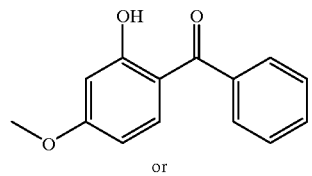

or

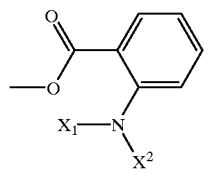

$(X_1=X_2=H)$, is described by G. Ciolfi et al., Vitis (1995), 34(3), 195–196.

For $R^3 =$

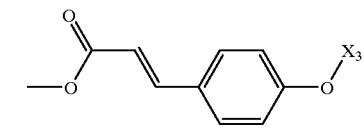

$X_3=CH_3$ the preparation is described by M. Majeric et al., Tetrahedron: Asymmetry (1996), 7(3), 815–824.

$X^7$ is H, $C_1$- to $C_8$-alkyl;

$R^4$ is $-(CO)_n-R^5$, $R^5$ is $C_1-C_{28}$-alkyl, n is 0 or 1, $R^6$ is $C_1-C_{22}$-alkyl, $R^7$, $R^8$ independently of one another are H or $CH_3$.

Preferred polymers are those in which the monomer units a to d have the following values:

a 15–50 b 5–70 c 30–80 d 0–20

Preferred monomers which form the unit a are those in which $R^1$ and $R^2$ independently of one another are H, $CH_3$, $C_2H_5$, particularly preferably $R^1$ and $R^2$ are $CH_3$.

Preferred monomers which form the unit b are those of the formula

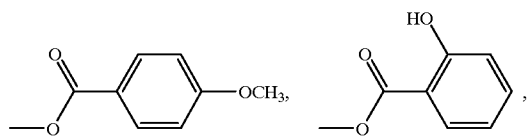

For $R^3 =$

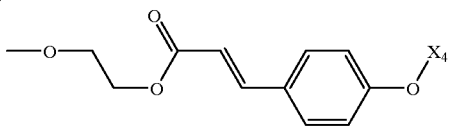

$X_4 = CH_3$ the preparation is described by T. G. Biryukova et al., Vysokomol. Soedin., Ser.B (1978), 20(8), 565–568.

For $R^3 =$

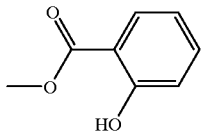

the preparation is described in U.S. Pat. No. 5,155,253 and U.S. Pat. No. 921,013.

Generally, the chromophore-bearing vinyl esters can be obtained by transesterification of the corresponding carboxyl-containing UV light-absorbing chromophores with vinyl acetate (see G. Heublein, B. Heublein, B. Heyroth, E. Brendel, Z. Chem. 19(1979) 104).

Generally, the chromophore-bearing vinyl ethers can be obtained by reaction of the OH-bearing UV light-absorbing chromophores with acetylene (see Organikum, Deutscher Verlag der Wissenschaften, Berlin, 1979, p. 338).

Among the monomers which form the unit c, those where $R^4 = -CO-R^9$ are preferred, $R^9$ being a branched alkyl having 6 to 12 C atoms, in particular

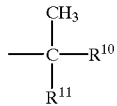

and $R^{10}$ and $R^{11}$ together comprising 6 to 7 C atoms.

Among the monomers which form the unit d, those where $R^6$ is $C_4$- to $C_{18}$-alkyl, in particular tert-butyl, 2-ethylhexyl or lauryl, are preferred.

The polymers according to the invention are prepared by subjecting the monomers which form the corresponding units a–d to free-radical polymerization under the customary conditions.

Suitable solvents are the customary organic solvents, in particular alcohols such as ethanol, isopropanol, butanol, esters such as ethyl acetate and butyl acetate, ketones such as acetone, methyl ethyl ketone and cyclohexanone, ethers such as tetrahydrofuran and methyl tert-butyl ether and alkanes such as hexane, heptane, cyclohexane and octane. Polymerization in a cosmetic oil such as paraffin oil, esters of benzoic acid with long-chain fatty alcohols, esters of glycerol with long-chain fatty acids, 2-octyldodecanol, isostearyl alcohol or esters of 2-ethylhexanoic acid with long-chain fatty alcohols is also advantageous. An ester of benzoic acid and $C_{12}$–$C_{16}$-alcohols is particularly preferred here. Polymerization in water is also possible, by emulsifying the monomers in water and polymerizing using a water-soluble initiator.

Suitable initiators are azo initiators such as, for example, azoisobutyronitrile and peroxides such as, for example, dibenzoyl peroxide, tertiary-butyl 2-ethylperhexanoate or peroxodisulfates. The reaction temperature is from 30 to 160° C., preferably 80 to 120° C.

As a rule, the polymers according to the invention have a molecular weight of from 2000 to 50,000, preferably from 4000 to 20,000 g/mol.

The polymer obtained is then formulated with auxiliaries and additives customary in cosmetics, depending on the intended use. Examples of suitable auxiliaries and additives for sunscreen compositions are described in W. Umbach, Kosmetik, Georg-Thieme-Verlag Stuttgart, 1988.

Beside the polymer-bound UV absorbers, the cosmetic compositions can also contain other soluble UV absorbers.

Preferably, other UV absorbers admixed are those which complement the absorption range of the polymer-bound UV absorber such that a protection which is as effective as possible over a wide UV range is achieved.

In particular, a good UV protection is achieved by addition of a soluble UV-A absorber in combination with the polymer-bound UV-B absorber.

The cosmetic compositions according to the invention are distinguished by their high water resistance, good skin tolerability and low skin penetration. They also have a good stability to hydrolysis, excellent oil solubility and high extinction.

The invention is further illustrated by the following examples.

EXAMPLE 1

Preparation of a Lipophilic UV Light-absorbing Polymer 20 g of butyl acetate are initially introduced under nitrogen and heated to 100° C. In the course of 2 h, a solution of 8 g of vinyl dimethylaminobenzoate in 32 g of vinyl neononanoate and a solution of 0.4 g of t-butyl peroxy-2-ethylhexanoate in 10 g of butyl acetate are metered in from separate vessels. After completion of the addition of the two solutions, the mixture is stirred at 100° C. for 4 h. After cooling, the solution is poured into 800 ml of ethanol and the precipitated polymer is removed by filtration.

Yield: 21 g Softening point: 115 to 118° C. GPC: Mn=14,000 g/mol, polydispersity=2.30 UV: 310 nm, $E^1_1 = 346$

EXAMPLE 2

Preparation of a Lipophilic UV Light-absorbing Polymer 20 g of butyl acetate are initially introduced under nitrogen and heated to 100° C. In the course of 2 h, a solution of 12 g of vinyl dimethylaminobenzoate in 28 g of vinyl neononanoate in 20 g of butyl acetate and a solution of 0.4 g of t-butyl peroxy-2-ethyl-hexanoate in 10 g of butyl acetate are metered in from separate vessels. After completion of the addition of the two solutions, the mixture is stirred at 100° C. for 4 h. After cooling, the solution is poured into 1000 ml of methanol and the precipitated polymer is removed by filtration.

Yield: 19.1 g Softening point: 98 to 102° C. GPC: Mn=8900 g/mol, polydispersity=2.27 UV: 308 nm, $E^1_1 = 503$

EXAMPLE 3

Preparation of a Lipophilic UV Light-absorbing Polymer 20 g of butyl acetate are initially introduced under nitrogen and heated to 100° C. In the course of 2 h, a solution of 16 g of vinyl dimethylaminobenzoate in 24 g of vinyl neononanoate and a solution of 0.4 g of t-butyl peroxy-2-ethylhexanoate in 10 g of butyl acetate are metered in from separate vessels. After completion of the addition of the two solutions, the mixture is stirred at 100° C. for 4 h. After cooling, the solution is poured into 1000 ml of ethanol and the precipitated polymer is removed by filtration.

Yield: 10.9 g Softening point: 107 to 110° C. GPC: Mn=9400 g/mol, polydispersity=1.94 UV: 308 nm, $E^1_1 = 606$ General preparation procedure for the preparation of emulsions for cosmetic purposes All oil-soluble constituents are heated to 85° C. in a stirring vessel. When all constituents have melted or are present as a liquid phase, the water phase is incorporated with homogenization. The emulsion is cooled to about 40° C. with stirring, perfumed, homogenized and then cooled to 25° C. with continuous stirring.

Preparations

EXAMPLE 4
Composition for Lip Care

| | |
|---|---|
| to 100 | Eucerinum anhydricum |
| 10.00 | glycerol |
| 10.00 | titanium dioxide |
| 0.5–10 | polymer from Example 1 |
| 8.00 | octyl methoxycinnamate |
| 5.00 | zinc oxide |
| 4.00 | castor oil |
| 4.00 | pentaerythrityl stearate/caprate/caprylate adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |

EXAMPLE 5
Composition for Lip Care

| | |
|---|---|
| to 100 | Eucerinum anhydricum |
| 10.00 | glycerol |
| 10.00 | titanium dioxide |
| 0.5–10 | polymer from Example 1 |
| 5.00 | butylmethoxydibenzoylmethane |
| 5.00 | zinc oxide |
| 4.00 | castor oil |
| 4.00 | pentaerythrityl stearate/caprate/caprylate adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |

EXAMPLE 6
Composition for Sunblock with Micropigments

| | |
|---|---|
| to 100 | water |
| 5.00 | butylmethoxydibenzoylmethane |
| 6.00 | PEG-7 hydrogenated castor oil |
| 6.00 | titanium dioxide |
| 0.5–10 | polymer from Example 3 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

EXAMPLE 7
Composition for Sunblock with Micropigments

| | |
|---|---|
| to 100 | Wasser |
| 10.00 | octyl methoxycinnamate |
| 6.00 | PEG-7 hydrogenated castor oil |
| 6.00 | titanium dioxide |
| 0.5–10 | Polymer from Example 2 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

EXAMPLE 8
Fat-free Gel

| | |
|---|---|
| to 100 | water |
| 8.00 | octyl methoxycinnamate |
| 7.00 | titanium dioxide |
| 0.5–10 | polymer from Example 2 |
| 5.00 | glycerol |
| 5.00 | PEG-25 PABA |
| 1.00 | 4-methylbenzylidenecamphor |
| 0.40 | acrylate C10-C30 alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

EXAMPLE 9
Fat-free Gel

| | |
|---|---|
| to 100 | water |
| 8.00 | octyl methoxycinnamate |
| 7.00 | titanium dioxide |
| 0.5–10 | polymer from Example 1 |
| 5.00 | glycerol |
| 5.00 | PEG-25 PABA |
| 1.00 | butylmethoxydibenzoylmethane |
| 0.40 | acrylate C10-C30 alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

EXAMPLE 10
Sun Cream

| | |
|---|---|
| to 100 | water |
| 8.00 | octyl methoxycinnamate |
| 8.00 | titanium dioxide |

| | |
|---|---|
| 6.00 | PEG-7 hydrogenated castor oil |
| 0.5–10 | polymer from Example 3 |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

EXAMPLE 11

Sun Cream

| | |
|---|---|
| to 100 | water |
| 8.00 | octyl methoxycinnamate |
| 8.00 | titanium dioxide |
| 6.00 | PEG-7 hydrogenated castor oil |
| 0.5–10 | polymer from Example 2 |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

EXAMPLE 12

Sun Cream, Water-resistant

| | |
|---|---|
| to 100 | water |
| 4.00 | butylmethoxydibenzoylmethane |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 0.5–10 | polymer from Example 1 |
| 4.00 | glycerol |
| 3.00 | jojoba oil |
| 2.00 | 4-methylbenzylidenecamphor |
| 2.00 | titanium dioxide |
| 1.50 | PEG-45/dodecyl glycol copolymer |
| 1.50 | dimethicone |
| 0.70 | magnesium sulfate |
| 0.50 | magnesium stearate |
| 0.15 | fragrance |

EXAMPLE 13

Sun Cream, Water-resistant

| | |
|---|---|
| to 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 0.5–10 | polymer from Example 2 |
| 4.00 | glycerol |
| 3.00 | jojoba oil |
| 2.00 | 4-methylbenzylidenecamphor |
| 2.00 | titanium dioxide |
| 1.50 | PEG-45/dodecyl glycol copolymer |
| 1.50 | dimethicone |
| 0.70 | magnesium sulfate |
| 0.50 | magnesium stearate |
| 0.15 | fragrance |

EXAMPLE 14

Sun Milk

| | |
|---|---|
| to 100 | water |
| 10.00 | mineral oil |
| 6.00 | PEG-7 hydrogenated castor oil |
| 5.00 | isopropyl palmitate |
| 3.50 | butylmethoxydibenzoylmethane |
| 0.5–10 | polymer from Example 2 |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 0.30 | glycerol |
| 0.25 | methylparaben |
| 0.15 | propylparaben |
| 0.05 | tocopherol |

EXAMPLE 15

Sun Milk

| | |
|---|---|
| to 100 | water |
| 10.00 | mineral oil |
| 6.00 | PEG-7 hydrogenated castor oil |
| 5.00 | isopropyl palmitate |
| 3.50 | octyl methoxycinnamate |
| 0.5–10 | polymer from Example 1 |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 0.30 | glycerol |
| 0.25 | methylparaben |
| 0.15 | propylparaben |
| 0.05 | tocopherol |

EXAMPLE 16

Sun Cream, Water-resistant

| | |
|---|---|
| to 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 0.5–10 | polymer from Example 1 |
| 0.5–10 | polymer from Example 3 |

-continued

| | |
|---|---|
| 4.00 | glycerol |
| 3.00 | jojoba oil |
| 2.00 | butylmethoxybenzoylmethane |
| 2.00 | titanium dioxide |
| 1.50 | PEG-45/dodecyl glycol copolymer |
| 1.50 | dimethicone |
| 0.70 | magnesium sulfate |
| 0.50 | magnesium stearate |
| 0.15 | fragrance |

We claim:

1. A polymeric UV absorber comprising the units shown in brackets in schematized formula I

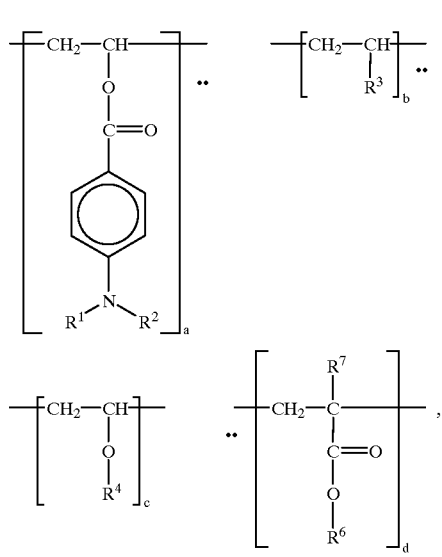

wherein
the sequence of the units is arbitrary, the sum of a+b+c+d=100 and
a is a percentage value from 5 to 95,
b is a percentage value from 0 to 70,
c is a percentage value from 5 to 95, and
d is a percentage value from 0 to 70;
$R^1$, $R^2$ independently of one another are H or $C_1$–$C_8$-alkyl;
$R^3$ is

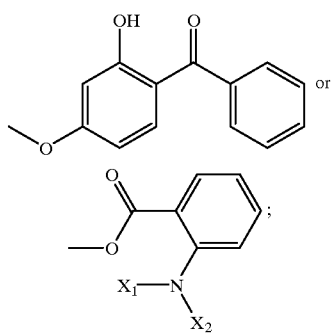

$X^1$, $X^2$ independently of one another are H, $C_1$–$C_8$-alkyl, or

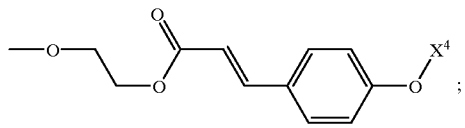

$X^3$ is H, $C_1$–$C_8$-alkyl, or

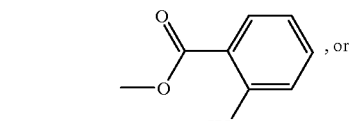

$X^4$ is H, $C_1$–$C_8$-alkyl,

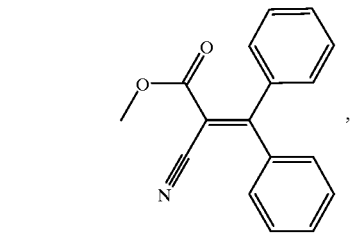

$X^5$, $X^6$ independently of one another are H, $C_1$–$C_8$-alkyl,

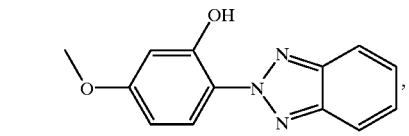

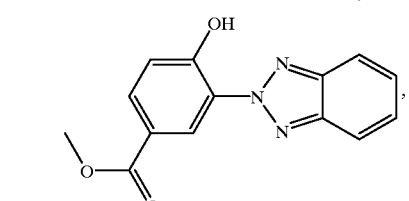

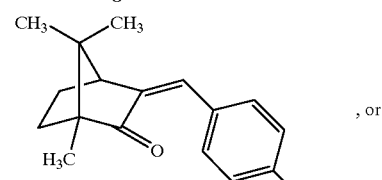

-continued

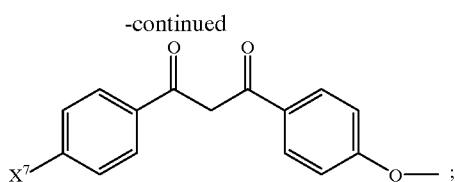

$X^7$ is H or $C_1$- to $C_8$-alkyl;
is $-(CO)_n-R^5$;
$R^5$ is $C_1-C_{28}$-alkyl;
n is 0 or 1;
$R^6$ is $C_1-C_{22}$-alkyl; and
$R^7$, $R^8$ independently of one another are H or $CH_3$.

2. A polymer as claimed in claim 1, where
$R^4$ is $-CO-R^9$,
$R^9$ is a branched alkyl having 6 to 12 C atoms.

3. A polymer as claimed in claim 2, where $R^4$ is

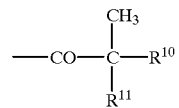

$R^{10}$, $R^{11}$ are alkyl, with the proviso that $R^{10}+R^{11}$ comprises 6 to 7 C atoms.

4. A polymer as claimed in claim 1, where
a is a percentage value from 15 to 50,
b is a percentage value from 0 to 70,
c is a percentage value from 30 to 80,
d is a percentage value from 0 to 70,
$R^6$ is $C_4$- to $C_{18}$-alkyl.

* * * * *

UNITED STATES PATENT AND TRADEMARK OFFICE
CERTIFICATE OF CORRECTION

PATENT NO. : 6,143,850
DATED : November 7, 2000
INVENTOR(S) : Keller et al.

Page 1 of 1

It is certified that error appears in the above-identified patent and that said Letters Patent is hereby corrected as shown below:

Column 13,
Line 2, after the formula, before "is" insert -- $R^4$ --.

Signed and Sealed this

Twenty-eighth Day of August, 2001

Attest:

NICHOLAS P. GODICI
Acting Director of the United States Patent and Trademark Office Attesting Officer